(12) United States Patent
Vasdev et al.

(10) Patent No.: US 10,280,152 B2
(45) Date of Patent: May 7, 2019

(54) IMAGING OF GLYCOGEN SYNTHASE KINASE 3

(71) Applicant: The General Hospital Corporation, Boston, MA (US)

(72) Inventors: Neil Vasdev, Cambridge, MA (US); Huan Steven Liang, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 3 days.

(21) Appl. No.: 15/563,022

(22) PCT Filed: Mar. 30, 2016

(86) PCT No.: PCT/US2016/025003
§ 371 (c)(1),
(2) Date: Sep. 29, 2017

(87) PCT Pub. No.: WO2016/160985
PCT Pub. Date: Oct. 6, 2016

(65) Prior Publication Data
US 2018/0370949 A1    Dec. 27, 2018

Related U.S. Application Data

(60) Provisional application No. 62/139,973, filed on Mar. 30, 2015.

(51) Int. Cl.
    *A61K 51/04*    (2006.01)
    *C07D 401/14*   (2006.01)
    *C07D 413/12*   (2006.01)
    *C07D 417/14*   (2006.01)

(52) U.S. Cl.
CPC ........ *C07D 401/14* (2013.01); *A61K 51/0463* (2013.01); *A61K 51/0474* (2013.01); *C07D 413/12* (2013.01); *C07D 417/14* (2013.01)

(58) Field of Classification Search
CPC .. C07D 401/14; C07D 413/12; C07D 417/14; A61K 51/0463; A61K 51/0474
USPC ...................................................... 514/340
See application file for complete search history.

(56) References Cited

U.S. PATENT DOCUMENTS

2009/0285756 A1   11/2009   Karimi et al.
2011/0060011 A1    3/2011   Brown et al.
2012/0021074 A1    1/2012   Burgey et al.

FOREIGN PATENT DOCUMENTS

EP    2009/117421    9/2009
WO    2008/070739    6/2008

OTHER PUBLICATIONS

International Search Report and Written Opinion dated Jun. 24, 2016 in international application No. PCT/US2016/025003, 16 pgs.
Pubchem. CID 60148521. Sep. 4, 2012, pp. 1-8 [online], [retrieved on May 14, 2016]. Retrieved from the Internet <URL: https://pubchem.ncbi.nlm.nih.gov/compound/60148521#section=Top>; p. 3, formula.
Pubchem. MolPort-028-298-436. Dec. 1, 2013; pp. 1-10 [onlirie], [retrieved on May 14, 2016]. Retrieved from the Internet <URL: https://pubchem.ncbi.nlm.nih.gov/compound/71988186#section=Top>; p. 3, formula.
Bohnen et al., "Effectiveness and Safety of 18F-FDG PET in the Evaluation of Dementia: A Review of the Recent Literature," J. Nucl. Med, 2012, 53:59-71.
Cohen and Goedert, "Gsk3 Inhibitors: Development and Therapeutic Potential," Nat. Rev. Drug Discov, 2004, 3:479-487.
Cole et al., "Synthesis and evaluation of [11C]PyrATP-1, a novel radiotracer for PET imaging of glycogen synthase kinase-3β (GSK-3β)," Nuclear Medicine and Biology, 2014, 41:507-512.
DaRocha-Souto et al., "Activation of glycogen synthase kinase-3 beta mediates β-amyloid induced neuritic damage in Alzheimer's disease," Neurobiol. Dis, Jan. 2012, 45:425.
Fuster-Matanzo et al., "Different Susceptibility to Neurodegeneration of Dorsal and Ventral Hippocampal Dentate Gyrus: A Study with Transgenic Mice Overexpressing GSK3β," PLoS ONE, 2011, 6:e27262.
Haar et al., "Structure of GSK3β reveals a primed phosphorylation mechanism," Nat. Struct. Mol. Bio, 2001, 8:593-596.
Hernandez et al., "Spatial learning deficit in transgenic mice that conditionally over-express GSK-3β in the brain but do not form tau filaments," J. Neurochem, Dec. 2002, 83:1529-1533.
Hicks et al., "Radiolabeled Small Molecule Protein Kinase Inhibitors for Imaging with PET or SPECT," Molecules, 2010, 15:8260.
Hicks et al., "Towards the preparation of radiolabeled 1-aryl-3-benzyl ureas: Radiosynthesis of [11C-carbonyl] AR-A014418 by [11C]CO2 fixation," Bioorganic & Medicinal Chemistry Letters, Mar. 2012, 22:2099-2101.
Holland et al., "Alternative approaches for PET radiotracer development in Alzheimer's disease: imaging beyond plaque," Journal of Labelled Compounds and Radiopharmaceuticals, Apr. 2014, 57:323-331.
Hooper et al., "The GSK3 hypothesis of Alzheimer's disease," J. Neurochem, Mar. 2008, 104:1433-1439.
Hurtado et al., "Selectively Silencing GSK-3 Isoforms Reduces Plaques and Tangles in Mouse Models of Alzheimer's Disease," J. Neurosci, May 2012, 32:7392-7402.
International Preliminary Report on patentability in International Application No. PCT/US2016/025003, dated Oct. 12, 2017.

(Continued)

*Primary Examiner* — Kristin A Vajda
(74) *Attorney, Agent, or Firm* — Fish & Richardson P.C.

(57) ABSTRACT

Provided herein are radiolabelled compounds useful for imaging GSK-3 kinase. An exemplary radiolabelled compound provided herein is useful as a radiotracer for imaging GSK-3 kinase using PET imaging. Methods for preparing the radiolabelled compounds and diagnostic methods using the radiolabelled compounds are also provided.

15 Claims, 1 Drawing Sheet

(56) References Cited

OTHER PUBLICATIONS

Jope and Johnson, "The glamour and gloom of glycogen synthase kinase-3," Trends in Biochemical Sciences, Feb. 2004, 29:95-102.
Kumata et al., "Radiosynthesis and preliminary PET evaluation of glycogen synthase kinase 3β (GSK-3β) inhibitors containing [11C]methylsulfanyl, [11C]methylsulfinyl or [11C]methylsulfonyl groups," Bioorganic & Medicinal Chemistry Letters, Aug. 2015, 25:3230-3233.
Lei et al., "GSK-3 in Neurodegenerative Diseases," International Journal of Alzheimer's Disease, 2011, 2011:189246.
Leroy et al., "Increased level of active GSK-3β in Alzheimer's disease and accumulation in argyrophilic grains and in neurons at different stages of neurofibrillary degeneration," Neuropathology and Applied Neurobiology, 2007, 33:43-55.
Li et al., "Synthesis and Initial in Vivo Studies with [11C]SB-216763: The First Radiolabeled Brain Penetrative Inhibitor of GSK-3," ACS Medicinal Chemistry Letters, 2015, 6:548-552.
Llorens-Maritin et al., "GSK-3β, a pivotal kinase in Alzheimer disease," Frontiers in Molecular Neuroscience, May 2014, 7:46.
Lucas et al., "Decreased nuclear β-catenin, tau hyperphosphorylation and neurodegeneration in GSK-3β conditional transgenic mice," Embo. J, 2001, 20:27-39.
Marquie et al., "Validating novel tau PET tracer [F-18]-AV-1451 (T807) on postmortem brain tissue," Ann. Neural, Nov. 2015, 78: 787-800.
Martinez et al., "Lessons Learnt from Glycogen Synthase Kinase 3 Inhibitors Development for Alzheimer's Disease," Current Topics in Medicinal Chemistry, 2013, 13:1808-1819.
McGinnity et al. "Initial Evaluation of 18F-GE-179, a Putative PET Tracer for Activated N-Methyl D-Aspartate Receptors," J. Nucl. Med, 2014, 55:423-430.
Meijer et al., "Pharmacological inhibitors of glycogen synthase kinase 3," Trends in Pharmaceutical Sciences, Sep. 2004, 25:471-480.
Okamura and Yanai, "Florbetapir (18F), a PET imaging agent that binds to amyloid plaques for the potential detection of Alzheimer's disease," IDrugs, 2010, 13:890-899.
Rotstein et al., "11CO2 fixation: a renaissance in PET radiochemistry," Chem. Commun., Jun. 2013, 49:5621-5629.
Rowe and Villemagne, "Brain Amyloid Imaging," J. Nucl. Med. Technol, Feb. 2013, 41:11-18.
Sirerol-Piquer et al., "GSK3 β overexpression induces neuronal death and a depletion of the neurogenic niches in the dentate gyrus," Hippocampus, Aug. 2011, 21: 910-922.
Stephenson et al., "Iodonium Ylide—Mediated Radiofluorination of 18F-FPEB and Validation for Human Use," J. Nucl. Med, Mar. 2015, 56:489-492.
Takahashi et al., "Localization and developmental changes of tau protein kinase I/glycogen synthase kinase-3 beta in rat brain," Journal of Neurochemistry, Jul. 1994, 63:245-255.
Thome et al., "GSK-3 modulates cellular responses to a broad spectrum of kinase inhibitors," Nat. Chem. Biol, Jan. 2015, 11:58-63.
Vasdev et al., "Synthesis and ex vivo evaluation of carbon-11 labelled N-(4-methoxybenzyl)-N'-(5-nitro-1,3-thiazol-2-yl)urea ([11C]AR-A014418): A radiolabelled glycogen synthase kinase-3β specific inhibitor for PET studies," Bioorganic & Medicinal Chemistry Letters, Dec. 2005, 15:5270-5273.
Wager et al., "Moving beyond Rules: The Development of a Central Nervous System Multiparameter Optimization (CNS MPO) Approach to Enable Alignment of Druglike Properties," ACS Chemical Neuroscience, Mar. 2010, 1: 435-449.
Wang and Mandelkow, "Tau in physiology and pathology," Nat. Rev. Neurosci, 2016, 17:22-35.
Wang et al., "The first synthesis of [(11)C]SB-216763, a new potential PET agent for imaging of glycogen synthase kinase-3 (GSK-3)," Bioorganic & Medicinal Chemistry Letters, Jan. 2011, 21:245-249.
Wilson et al., "Utility of commercial radiosynthetic modules in captive solvent [11C]—methylation reactions," Journal of Labelled Compounds and Radiopharmaceuticals, Sep. 2009, 52:490-492.
Woodgett et al., In Glycogen Synthase Kinase 3 (GSK-3) and Its Inhibitors: Drug Discovery and Development; John Wiley and Sons, Inc.: Hoboken, New Jersey, 2006, p. 3.
Woodgett, "cDNA cloning and properties of glycogen synthase kinase-3," Methods Enzymol, 1991, 200:564-577.
Woodgett "Molecular cloning and expression of glycogen synthase kinase-3/factor A," EMBOJ. Aug. 1990, 9:2431-2438.

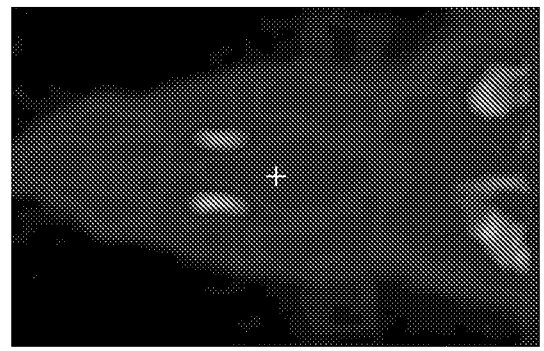
35-45 min
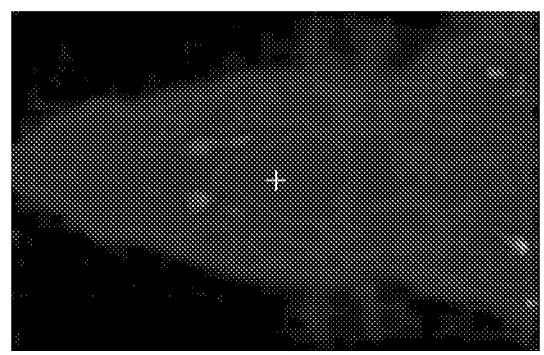
2-35 min
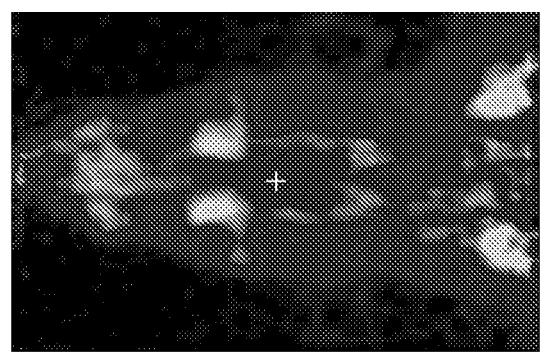
0-2 min

IMAGING OF GLYCOGEN SYNTHASE KINASE 3

CROSS-REFERENCE TO RELATED APPLICATIONS

This application is a 35 U.S.C. § 371 National Stage Application of International Application No. PCT/US2016/025003, filed Mar. 30, 2016, which claims priority to U.S. Provisional Application No. 62/139,973, filed Mar. 30, 2015. The entire content of each of these applications is hereby incorporated herein by reference.

TECHNICAL FIELD

This invention relates to radiolabelled compounds useful for imaging techniques, and more particularly to radiolabelled compounds that are useful for imaging GSK-3 kinase.

BACKGROUND

Glycogen synthase kinase 3 (GSK-3) is a serine and threonine kinase that regulates a plethora of physiological functions in the periphery and central nervous system ranging from differentiation and development, to metabolism, cell cycle regulation, and neuroprotection (see e.g., Woodgett et al., *EMBO J.* 1990, 9:2431; Woodgett et al., *In Glycogen Synthase Kinase 3 (GSK-3) and Its Inhibitors: Drug Discovery and Development*; John Wiley and Sons, Inc.: Hoboken, N.J., 2006, pg 3; Jope et al., *Trends in Biochemical Sciences*, 2004, 29:95; Meijer et al., *Trends in Pharmaceutical Sciences*, 2004, 25:471; Lei et al., *International Journal of Alzheimer's Disease*, 2011, 2011:9; and Thorne et al., *Nat. Chem. Biol.* 2015, 11:58). Two paralogues, GSK-3α (51 kDa) and GSK-3β (47 kDa) are known and there is high homology in their kinase domains (ca. 98% identical in their catalytic domains) (see e.g., Woodgett et al., *Methods Enzymol*, 1991, 200:564; and Harr et al., *Nat. Struct. Mol. Bio.* 2001, 8:593). GSK-3 plays a significant role in several pathologies including Alzheimer's disease (AD), bipolar disorder, schizophrenia, Huntington's disease, type-II diabetes, stroke, cardiac ischemia, age-related loss of bone and muscle, chronic inflammatory conditions, and in some cancers (see e.g., Martinez et al., *Current Topics in Medicinal Chemistry*, 2013, 13:1808).

Specifically for neurodegenerative diseases, molecular imaging of GSK-3 can indicate target engagement by GSK-3 therapeutics and offer a path to diagnostic agents that not only correlates with early cognitive impairment, but also increased tau hyperphosphorylation, (see e.g., Martinez et al., *Current Topics in Medicinal Chemistry*, 2013, 13:1808; Takahashi et al., *Journal of Neurochemistry*, 1994, 63:245); and Wang et al., *Nat. Rev. Neurosci.* 2016, 17:22) increased amyloid-β production (see e.g., DaRocha-Souto et al., *Neurobiol. Dis.* 2012, 45:425) and local plaque-associated glial-mediated inflammatory responses; all of which are hallmarks of AD and non-AD tauopathies. This has led to the GSK-3 Hypothesis of Alzheimer's Disease (see e.g., Hooper et al., *J. Neurochem*, 2008, 104:1433). GSK-3 plays a key role in AD evident from: (i) the abundance and dysregulation of GSK-3 in the AD brain (see e.g., Lucas et al., *Embo. J.* 2001, 20:27; Hernandez et al., *J. Neurochem*, 2002, 83:1529; Fuster-Matanzo et al., *PLoS ONE,* 2011, 6:e27262; Sirerol-Piquer et al., *Hippocampus*, 2011, 21:910; and Leroy et al., *Neuropathology and Applied Neurobiology*, 2007, 33:43), (ii) reduced tau phosphorylation (pTau) induced by treatment with GSK-3β inhibitors (see e.g., Hurtado et al., *J. Neurosci,* 2012, 32:7392) and, (iii) genetic studies suggesting GSK-3 is fundamental in the pathogenesis of sporadic and familial AD. The defining neuropathological lesions of AD are amyloid-β (Aβ) senile plaques and tau neurofibrillary tangles, both of which appear many years before the onset of symptoms of cognitive impairment (see e.g., Hurtado et al., *J. Neurosci,* 2012, 32:7392; and Llorens-Maritin et al., *Frontiers in Molecular Neuroscience*, 2014, 7:46). GSK-3β has been recognized as one of the principal kinases involved in phosphorylation of tau, an essential protein for stabilization of intracellular microtubules. The phenotypic forms of neurofibrillary tangles with fine structure composed of paired helical fragments are typically a result of tau aggregation induced by hyperphosphorylation of tau. Over-expression of GSK-3 has been studied extensively in transgenic animal models of AD and in AD patients, whose hippocampal brain regions have elevated GSK-3β expression and/or enzymatic activity (see e.g., Hurtado et al.). The role of GSK-3β in tau phosphorylation makes it a particularly attractive therapeutic target for AD and non-AD tauopathies (see e.g., Llorens-Maritin et al.).

The pertinence of GSK-3 in diverse diseases has led to long-standing, world-wide efforts by major pharmaceutical companies to develop small molecule inhibitors as therapeutics for this target (see e.g., Cohen et al., *Nat. Rev. Drug Discov.* 2004, 3:479). Clinical translation of potent GSK-3 therapeutics for neurodegenerative disease have faced three major hurdles: 1) poor GSK-3 selectivity over other central nervous system (CNS) targets and closely related kinases; 2) low blood-brain barrier (BBB) penetration and 3) chronic toxicity. A PET radiotracer for GSK-3 could aid the many ongoing clinical research efforts to develop GSK-3 targeted therapeutics by indicating the success and extent of engagement by GSK-3 inhibitors in the brain.

Development of a robust and reliable radiotracer for detecting biomarkers for dementias is among the most sought-after goals in nuclear medicine. Current clinical neuroimaging agents for AD are generally classified as: (i) enzyme trapped substrates (e.g., [$^{18}$F]FDG); Bohnen et al., *J. Nucl. Med.* 2012, 53:59) (ii) amyloid plaque or tau protein targeted tracers (e.g., [$^{18}$F]Amyvid, [$^{11}$C]PiB, [$^{18}$F]T807; Okamura et al., *IDrugs*, 2010, 13:890; Rowe et al., *J. Nucl. Med. Technol.* 2013, 41:11; Marquie et al., *Ann. Neurol.* 2015, 78, 787), (iii) neuroreceptor imaging probes (e.g., [$^{18}$F]FPEB, [$^{18}$F]GE179; Stephenson et al., *J. Nucl. Med.,* 2015, 56:489; and McGinnity et al. *J. Nucl. Med.* 2014, 55:423). While the advent of imaging and fluid biomarkers of brain β-amyloidosis has propelled the field forward and improved the ascertainment of early stages of AD, the levels of deposited Aβ do not relate robustly to the clinical phenotype. From a PET imaging perspective, despite substantial progress in AD biomarker development over the past decade, we do not yet have a radiotracer that combines two key properties: 1) positivity at an early stage of disease; and 2) good correlation with progression of symptoms and signs of the disease in AD and non-AD tauopathies.

Similar to the challenges for advancing a GSK-3 therapeutic for the CNS, the greatest obstacles for molecular neuroimaging of GSK-3 has been the lack of potent and highly selective small molecules with reasonable brain penetration that are capable of being radiolabelled. Our initial work on this target as a PET radiotracer for GSK-3 (see e.g., Vasdev et al., *Bioorganic & Medicinal Chemistry Letters,* 2005, 15:5270; and Hicks et al., *Molecules*, 2010, 15:8260) focused on the synthesis of $^{11}$C-labelled isotopologues of AR-A014418 (see e.g., Vasdev et al.; and Hicks et al., *Bioorganic & Medicinal Chemistry Letters*, 2012, 22:2099), and subsequently other laboratories explored different scaffolds. Only three other radiotracers for GSK-3 have been studied in vivo. [11C]SB-216763 showed good brain uptake in rodents and non-human primates (NHPs) but was not selective against other structurally similar kinases (see e.g., Wang et al., *Bioorganic & Medicinal Chemistry Letters*, 2011, 21:245; and Li et al., *ACS Medicinal Chemistry Letters*, 2015, 6:548). [11C]PyrATP-1[34] and 11C-oxadiazole[35] based radiotracers failed to show appreciable uptake in vivo (see e.g., Cole et al., *Nuclear Medicine and Biology*, 2014, 41:507; and Kumata et al., *Bioorganic & Medicinal Chemistry Letters*, 2015, 25:3230). None of the PET radiotracers for GSK-3 have yet proven to be successful for in vivo imaging studies with specificity and/or suitable brain uptake. Thus a striking need for PET neuroimaging of GSK-3 remains, specifically for clinical research applications in AD and non-AD tauopathies (see e.g., Holland et al., *Journal of Labelled Compounds and Radiopharmaceuticals*, 2014, 57:323).

SUMMARY

The present application provides, inter alia, a radiolabelled compound of Formula I, and various embodiments thereof:

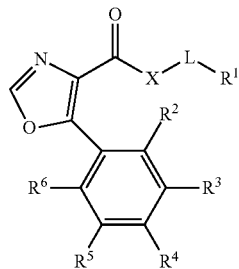

or a salt thereof, wherein:
X is selected from the group consisting of O and $NR^N$;
$NR^N$ is selected from the group consisting of H, $C_{1-6}$ alkyl, $C_{1-6}$ haloalkyl;
L is selected from the group consisting of $C_{1-6}$ alkylene and $C_{1-6}$ haloalkylene;
$R^1$ is selected from the group consisting of H, halo, $C_{1-6}$ alkyl, $C_{1-6}$ haloalkyl, $C_{1-6}$ alkoxy, $C_{1-6}$ haloalkoxy, and 5-10 membered heteroaryl;
$R^2$, $R^3$, $R^4$, $R^5$, and $R^6$ are each independently selected from the group consisting of H, halo, $C_{1-6}$ alkyl, $C_{1-6}$ haloalkyl, hydroxy, $C_{1-6}$ alkoxy, $C_{1-6}$ haloalkoxy, and $C_{1-6}$ alkylthio; and
wherein the compound of Formula I is radiolabelled.

The present disclosure provides a method of imaging GSK-3 kinase in a cell or tissue sample, the method comprising contacting the cell or tissue sample with the radiolabelled compound or salt thereof of Formula I, or any of the embodiments thereof, and subsequently imaging the cell or tissue sample.

The present disclosure provides a method of imaging GSK-3 kinase in a subject, comprising administering to the subject the radiolabelled compound or salt thereof of any one of claims 1 to 15, and subsequently imaging the subject.

The GSK-3 kinase can comprises GSK-3α and/or GSK-3β. The imaging can be, e.g., PET imaging or SPECT imaging.

The details of one or more embodiments of the invention are set forth in the accompa-nying drawings and the description below. Other features, objects, and advantages of the invention will be apparent from the description and drawings, and from the claims. All publications, patent applications, patents, sequences, database entries, and other references mentioned herein are incorporated by reference in their entirety. In case of conflict, the present specification, including definitions, will control.

DESCRIPTION OF DRAWINGS

FIG. 1 is a set of 3 Positron Emission Tomography images obtained using [11C]-labelled compound (1) in a rat.

DETAILED DESCRIPTION

It is appreciated that certain features described herein, which are, for clarity, described in the context of separate embodiments, can also be provided in combination in a single embodiment. Conversely, various features described herein which are, for brevity, described in the context of a single embodiment, can also be provided separately or in any suitable subcombination.

Unless defined otherwise, all technical and scientific terms used herein have the same meaning as is commonly understood by one of ordinary skill in the art to which this disclosure belongs. All patents, applications, published applications and other publications cited herein are incorporated by reference in their entirety. In the event that there is a plurality of definitions for terms cited herein, those in this section prevail unless otherwise stated.

For the terms "e.g.," and "such as," and grammatical equivalents thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise.

As used herein, the singular forms "a," "an," and "the" include plural referents unless the context clearly dictates otherwise.

Starting from a high-throughput screening hit, herein a potent GSK-3 inhibitor was identified [N-(3-(1H-1,2,4-triazol-1-yl)propyl)-5-(3-chloro-4-methoxyphenyl)oxazole-4-carboxamide; compound (1), PF-04802367 or PF-367) was identified with exceptional kinome selectivity that modulates phosphorylated tau levels in vivo in rodents.

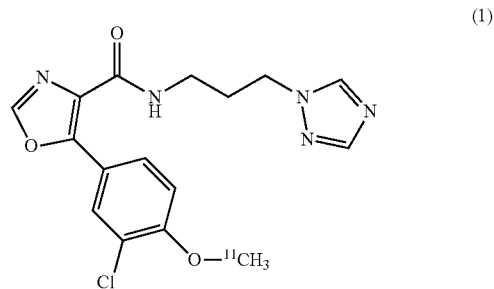 [SMILES: [11CH3]Oc1ccc(-c2ocnc2C(=O)NCCCn2cncn2)cc1Cl]

PET imaging studies using carbon-11 ($^{11}C$; $\beta^+$, $t_{1/2}$=20.4 min) labelled compound (1) in non-human primates have surprisingly found that radiolabelled compound (1) can be used as a promising diagnostic imaging agent for GSK-3 levels in the living brain and for probing signaling events mediated by this protein kinase.

Based on functional and competitive binding assays against a wide panel of protein kinases, we have shown that compound (1) represents one of the most selective inhibitor of GSK-3 that has been reported to date. X-ray crystal structure analysis and structure activity relationship suggest that compound (1) attains its potency and selectivity by forming strong cation-π interactions with a relatively rigid arginine at the ATP site of GSK-3β. Moreover, cellular assays targeting Wnt signaling pathway show a separation in doses required for efficacy (pTau modulation) vs. potential toxicity endpoints. An $^{11}$C-isotopologue of compound (1) was synthesized and preliminary PET imaging studies confirmed high brain permeability and specificity in the non-human primate brain. Compound (1) induced modulation of pTau may have potential therapeutic effects for several neurodegenerative diseases and represents an outstanding lead diagnostic neuroimaging agent for GSK-3. Our future work will also include further in vivo imaging studies with this tracer in non-human primates and testing this lead compound in GSK-3 models of AD by postmortem analysis.

I. Radiolabelled Compounds

The present application provides, inter alia, a radiolabelled compound of Formula I:

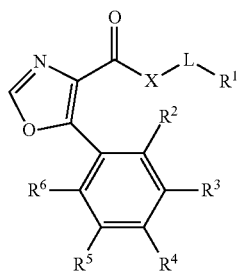

I or a salt thereof, wherein:
X is selected from the group consisting of O and $NR^N$;
$NR^N$ is selected from the group consisting of H, $C_{1-6}$ alkyl, $C_{1-6}$ haloalkyl;
L is selected from the group consisting of $C_{1-6}$ alkylene and $C_{1-6}$ haloalkylene;
$R^1$ is selected from the group consisting of H, halo, $C_{1-6}$ alkyl, $C_{1-6}$ haloalkyl, $C_{1-6}$ alkoxy, $C_{1-6}$ haloalkoxy, and a 5-10 membered heteroaryl group;
$R^2$, $R^3$, $R^4$, $R^5$, and $R^6$ are each independently selected from the group consisting of H, halo, $C_{1-6}$ alkyl, $C_{1-6}$ haloalkyl, hydroxy, $C_{1-6}$ alkoxy, $C_{1-6}$ haloalkoxy, and $C_{1-6}$ alkylthio.
wherein the compound of Formula I is radiolabelled.

As used herein, the term "radiolabelled" refers to a compound comprising at least one radioisotope (e.g., $^{11}$C, $^{18}$F, $^{123}$I, and the like) in an amount at least greater than the natural abundance of the isotope or radioisotope. For example, the radioisotope may be present at an abundance that is at least 100 times greater than its natural abundance.

In some embodiments, the compound is radiolabelled with a positron emitting radioisotope. Example positron emitting radioisotopes include, but are not limited to, In some embodiments, the positron emitter is selected from the group consisting of $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc $^{110m}$In, $^{118}$Sb, $^{120}$I, $^{121}$I, $^{122}$I, and $^{124}$I. In some embodiments, the compound is radiolabelled with a positron emitting radioisotope such as $^{11}$C, $^{13}$N, $^{15}$O, $^{18}$F or $^{124}$I. In some embodiments, the compound is radiolabelled with a positron emitting radioisotope selected from $^{11}$C, $^{18}$F, and $^{124}$I.

In some embodiments, the radiolabelled compound is radiolabelled with a gamma emitting radioisotope. Example gamma emitting radioisotopes include, but are not limited to, $^{60}$Co, $^{123}$I, $^{125}$I, $^{131}$I, $^{137m}$Ba, and $^{192}$Ir. In some embodiments, the radiolabelled compound is radiolabelled with a gamma emitting radioisotope such as $^{123}$I, $^{125}$I, or $^{131}$I. In some embodiments, the radiolabelled compound is radiolabelled with a gamma emitting radioisotope such as $^{123}$I.

In some embodiments, X is $NR^N$. In some embodiments, $R^N$ is H. In some embodiments, X is O.

In some embodiments, L is $C_{1-6}$ alkylene such as trimethylene (—$CH_2CH_2CH_2$—). In some embodiments, L is $C_{1-6}$ haloalkylene. In some embodiments, L is a $C_{1-6}$ haloalkylene selected from $C_{1-6}$ fluoroalkylene and $C_{1-6}$ iodoalkylene. In some embodiments, the $C_{1-6}$ fluoroalkylene is a $C_{1-6}$ [$^{18}$F]fluoroalkylene. In some embodiments, the $C_{1-6}$ iodoalkylene is a $C_{1-6}$ [$^{124}$I]iodoalkylene.

In some embodiments, at least one of $R^1$, $R^2$, $R^3$, $R^4$, $R^5$, and $R^6$ is radiolabelled. In some embodiments, at least one of $R^1$, $R^2$, $R^3$, $R^4$, $R^5$, and $R^6$ is radiolabelled with a positron emitting radioisotope. In some embodiments, at least one of $R^1$, $R^2$, $R^3$, $R^4$, $R^5$, and $R^6$ is radiolabelled with a positron emitting radioisotope selected from $^{11}$C, $^{18}$F, and $^{124}$I. In some embodiments, at least one of $R^1$, $R^2$, $R^3$, $R^4$, $R^5$, and $R^6$ is radiolabelled with a gamma emitting radioisotope. In some embodiments, at least one of $R^1$, $R^2$, $R^3$, $R^4$, R, and $R^6$ is radiolabelled with a gamma emitting radioisotope selected from $^{123}$I, $^{125}$I, and $^{131}$I.

In some embodiments, $R^1$ is selected from the group consisting of halo, $C_{1-6}$ haloalkyl, $C_{1-6}$ haloalkoxy, and a 5-6 membered heteroaryl group. In some embodiments, $R^1$ is selected from the group consisting of fluoro, $C_{1-6}$ fluoroalkyl, a $C_{1-6}$ fluoroalkoxy, and a 5-6 membered heteroaryl group. In some embodiments, $R^1$ is selected from the group consisting of fluoro, fluoroethyl, fluoropropyl, —$CH_2CH_2OCH_2CH_2F$, —$CH_2CH_2OCH_2CH_2OCH_2CH_2F$, and a triazole (such as a 1H-1,2,4-triazole) ring. In some embodiments, $R^1$ is selected from the group consisting of [$^{18}$F], [$^{18}$F]fluoroethyl, [$^{18}$F]fluoropropyl, —$CH_2CH_2OCH_2CH_2$[$^{18}$F], —$CH_2CH_2OCH_2CH_2OCH_2CH_2$[$^{18}$F], and a triazole (such as a 1H-1,2,4-triazole) ring.

In some embodiments, at least one of $R^2$, $R^3$, $R^4$, $R^5$, and $R^6$ is selected from the group consisting of halo, $C_{1-6}$ alkyl, $C_{1-6}$ haloalkyl, hydroxy, $C_{1-6}$ alkoxy, $C_{1-6}$ haloalkoxy, and $C_{1-6}$ alkylthio. In some embodiments, at least two of $R^2$, $R^3$, $R^4$, $R^5$, and $R^6$ are selected from the group consisting of halo, $C_{1-6}$ alkyl, $C_{1-6}$ haloalkyl, hydroxy, $C_{1-6}$ alkoxy, $C_{1-6}$ haloalkoxy, and $C_{1-6}$ alkylthio. In some embodiments, the halo is Cl, F, or I. In some embodiments, the halo is a positron emitting radioisotope. In some embodiments, the halo is $^{18}$F. In some embodiments, the $C_{1-6}$ alkyl, $C_{1-6}$ haloalkyl, $C_{1-6}$ alkoxy, $C_{1-6}$ haloalkoxy, $C_{1-6}$ alkylthio comprise at least one radioisotope. In some embodiments, the $C_{1-6}$ alkyl, $C_{1-6}$ haloalkyl, $C_{1-6}$ alkoxy, $C_{1-6}$ haloalkoxy, $C_{1-6}$ alkylthio comprise at least one positron emitting radioisotope selected from $^{11}$C, $^{18}$F, and $^{124}$I. In some embodiments, the halo, $C_{1-6}$ haloalkyl and $C_{1-6}$ haloalkoxy comprise at least one gamma emitting radioisotope. In some embodiments, the $C_{1-6}$ haloalkyl and $C_{1-6}$ haloalkoxy comprise at least one gamma emitting radioisotope selected from $^{123}I$, $^{125}I$, and $^{131}I$.

In some embodiments, $R^2$ is hydrogen.

In some embodiments, $R^3$ is hydrogen or halo. In some embodiments, $R^3$ is hydrogen or chloro.

In some embodiments, $R^4$ is selected from the group consisting of hydrogen, halo, hydroxy, $C_{1-6}$ alkoxy, and $C_{1-6}$ haloalkoxy. In some embodiments, $R^4$ is $C_{1-6}$ alkoxy. In some embodiments, $R^4$ is a $[^{11}C]$-radiolabelled $C_{1-6}$ alkoxy. In some embodiments, $R^4$ is —$O^{11}CH_3$.

In some embodiments, $R^5$ is hydrogen or halo. In some embodiments, $R^5$ is hydrogen or chloro.

In some embodiments, $R^6$ is hydrogen.

In some embodiments, $R^2$, $R^3$, and $R^6$ are each hydrogen.

In some embodiments, the radiolabelled compound is a compound selected from the group consisting of Formulae I-A, I-B, I-C, I-D, I-E, I-F, I-G, I-H, I-I, I-J, I-K, I-L, I-M, I-N, and I-O:

I-A
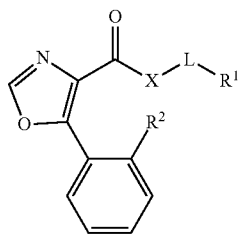

I-B
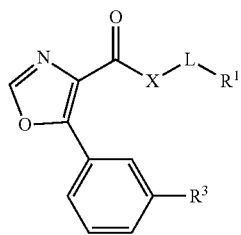

I-C
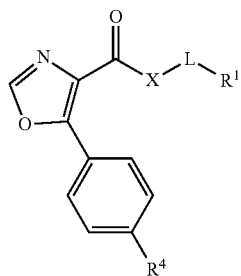

I-D
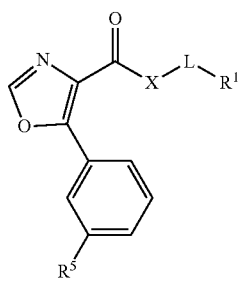

I-E
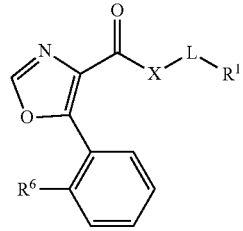

I-F
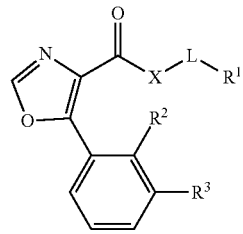

I-G
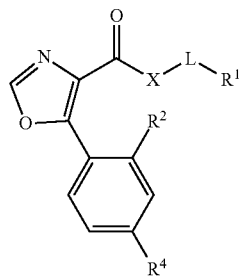

I-H
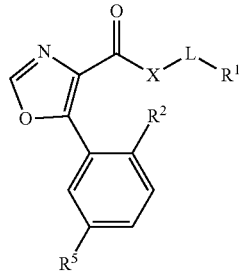

I-I
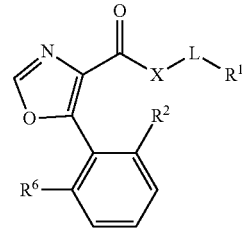

I-J
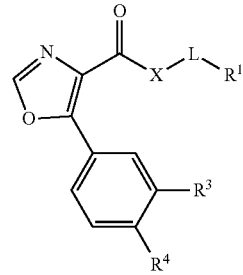

or a salt thereof, wherein groups X, L, R², R³, R⁴, R⁵, and R⁶ are as defined above.

In some embodiments, the radiolabelled compound is a compound selected from the group consisting of Formulae II-A, II-B, II-C, II-D, II-E, II-F, II-G, II-H, II-I, II-J, II-K, II-L, II-M, II-N, and II-O:

or a salt thereof, wherein groups X, L, R¹, R², R³, R⁴, R⁵, and R⁶ are as defined above.

In some embodiments, the radiolabelled compound is a compound of Formula II:

-continued
II-E
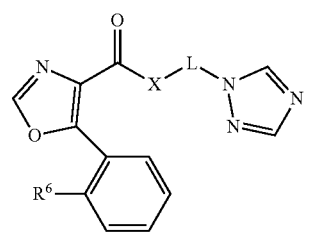
II-F
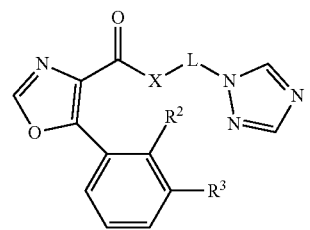
II-G
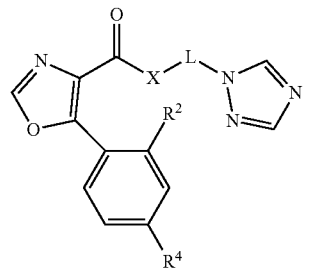
II-H
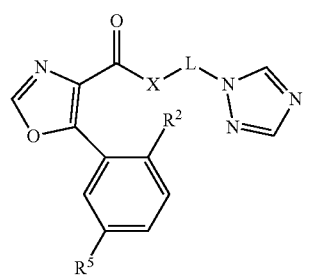
II-I
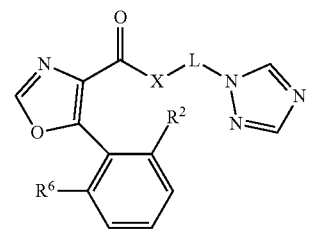
II-J
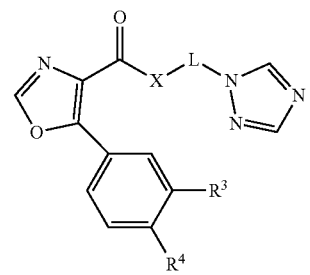
II-K
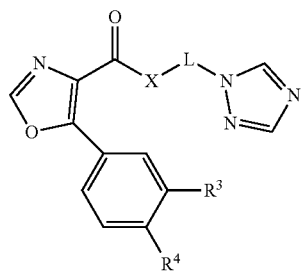
II-L
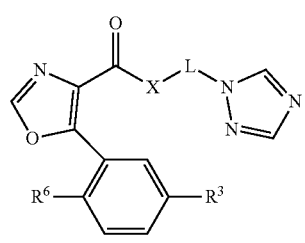
II-M
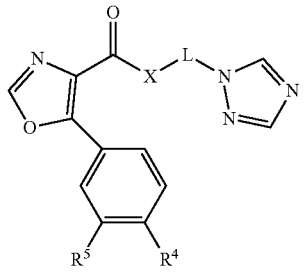
II-N
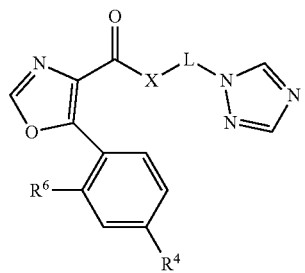
II-O
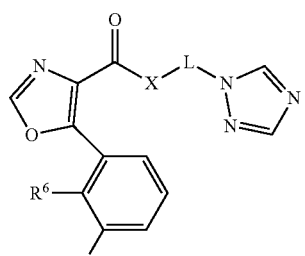
or a salt thereof, wherein groups X, L, $R^2$, $R^3$, $R^4$, $R^5$, and $R^6$ are as defined above.
In some embodiments, the radiolabelled compound of Formula I is a compound of Formula II-M:

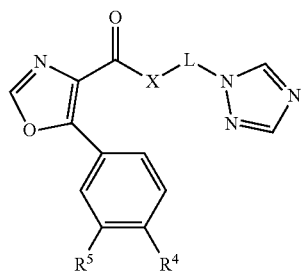

II-M or a salt thereof, wherein groups X, L, R⁴, and R⁵ are as defined above.

In some embodiments, the radiolabelled compound is a compound of Formula III:

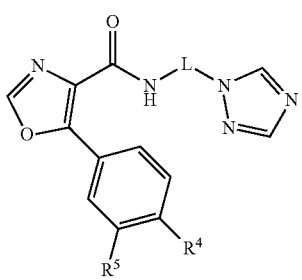

III or a salt thereof, wherein:

L is selected from the group consisting of $C_{1-6}$ alkylene and $C_{1-6}$ haloalkylene;

R⁴ and R⁵ are each independently selected from the group consisting of halo, $C_{1-6}$ alkyl, $C_{1-6}$ haloalkyl, hydroxy, $C_{1-6}$ alkoxy, $C_{1-6}$ haloalkoxy, and $C_{1-6}$ alkylthio.

In some embodiments, L is $C_{1-6}$ alkylene such as trimethylene (—CH₂CH₂CH₂—). In some embodiments, L is $C_{1-6}$ haloalkylene. In some embodiments, L is a $C_{1-6}$ haloalkylene selected from $C_{1-6}$ fluoroalkylene and $C_{1-6}$ iodoalkylene. In some embodiments, the $C_{1-6}$ fluoroalkylene is a $C_{1-6}$ [¹⁸F]fluoroalkylene. In some embodiments, the $C_{1-6}$ iodoalkylene is a $C_{1-6}$ [¹²⁴I]iodoalkylene.

In some embodiments, R⁴ is selected from the group consisting of hydrogen, halo, hydroxy, $C_{1-6}$ alkoxy, and $C_{1-6}$ haloalkoxy. In some embodiments, R⁴ is $C_{1-6}$ alkoxy. In some embodiments, R⁴ is a [¹¹C]-radiolabelled $C_{1-6}$ alkoxy. In some embodiments, R⁴ is —O¹¹CH₃.

In some embodiments, R⁵ is hydrogen or halo. In some embodiments, R⁵ is hydrogen or chloro.

In some embodiments, the radiolabelled compound of Formula I is selected from the group consisting of compounds of the following formulae (2)-(44):

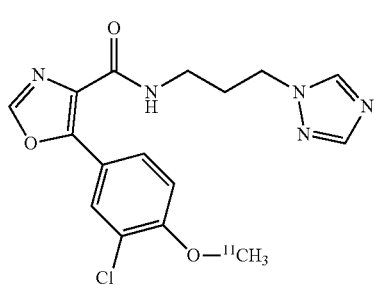

(2)

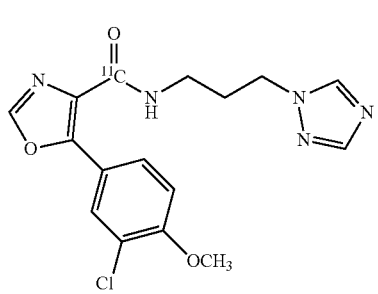

(3)

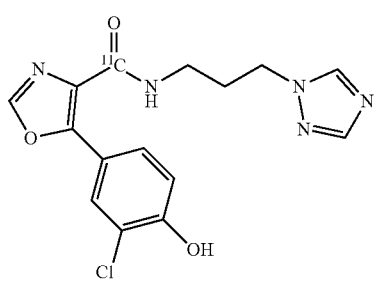

(4)

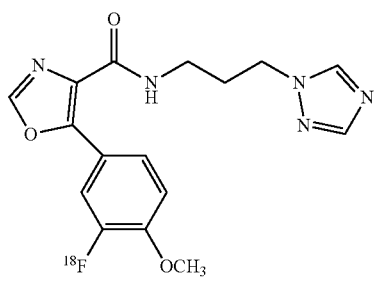

(5)

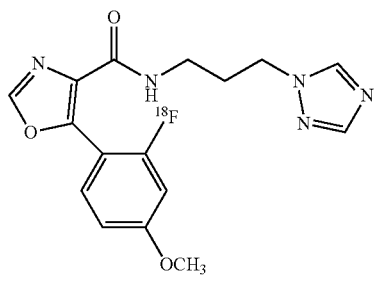

(6)

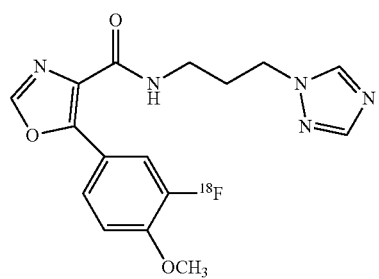
(7)
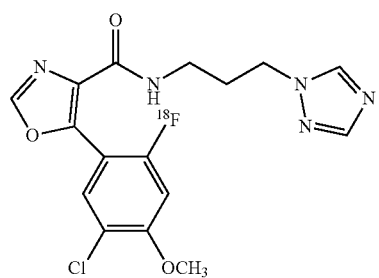
(8)
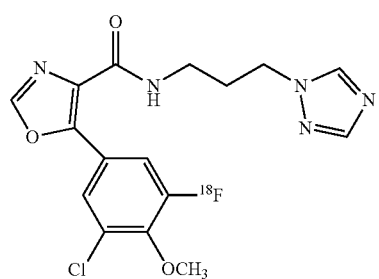
(9)
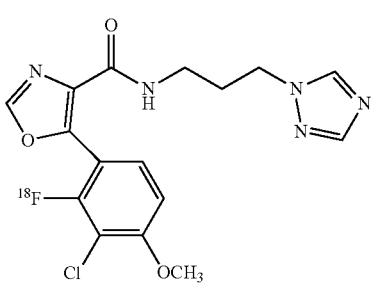
(10)
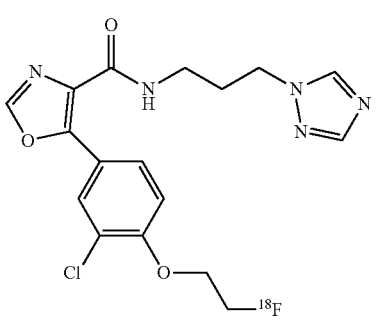
(11)
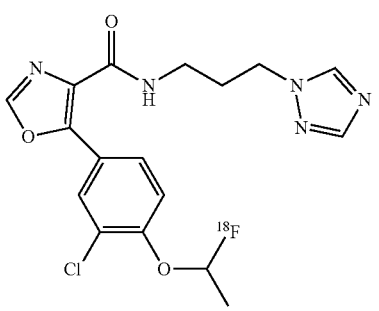
(12)
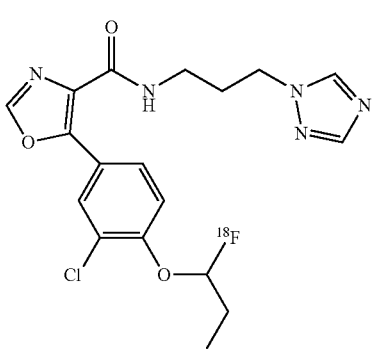
(13)
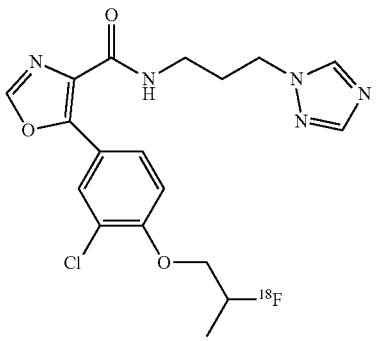
(14)
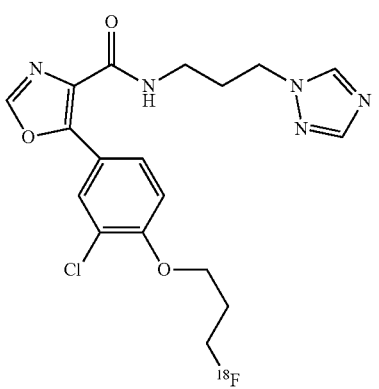
(15)

-continued
(16)
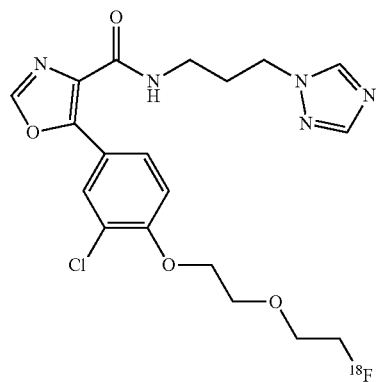
(17)
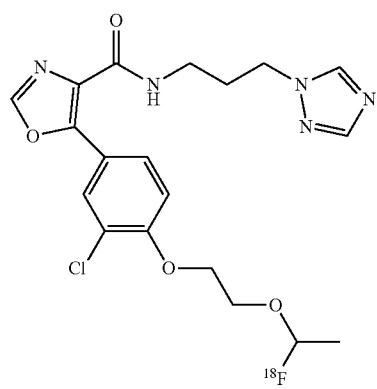
(18)
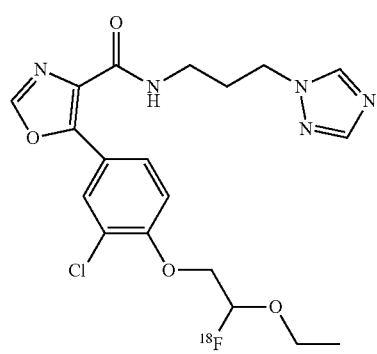
(19)
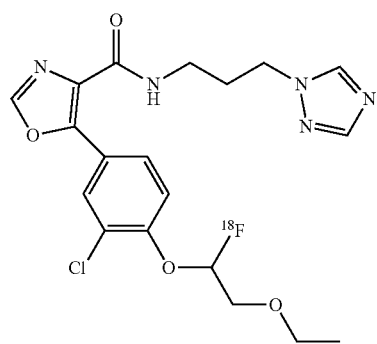
-continued
(20)
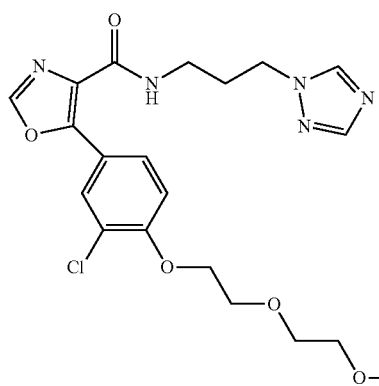
(21)
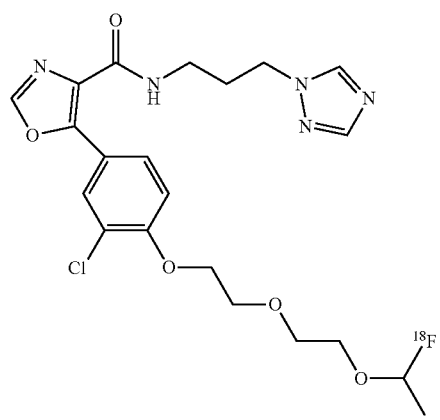
(22)
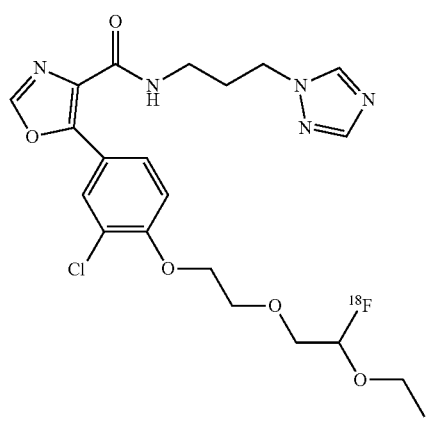

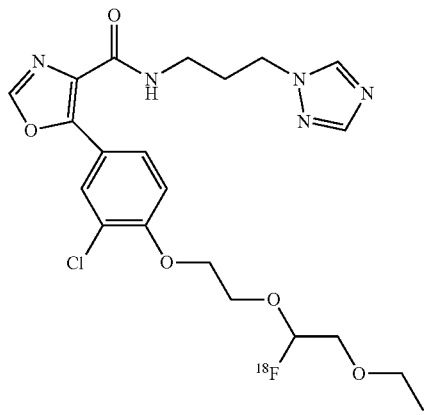
(23)
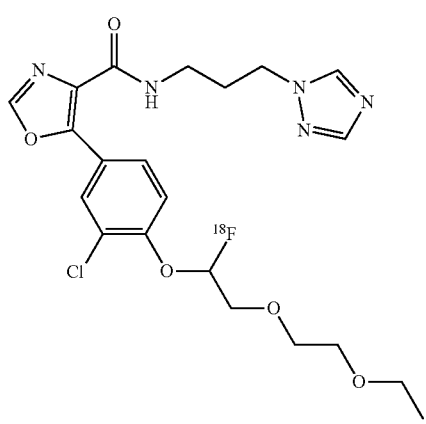
(24)
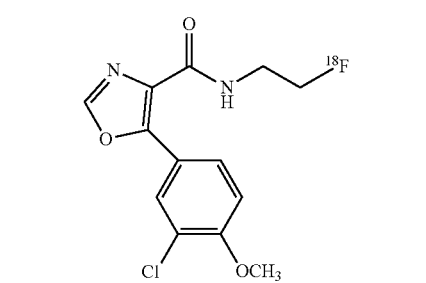
(25)
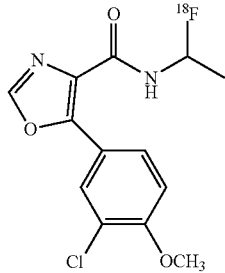
(26)
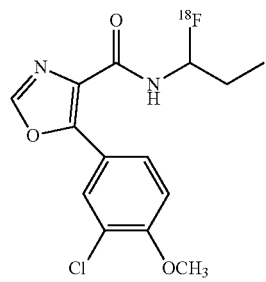
(27)
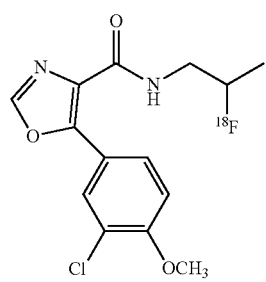
(28)
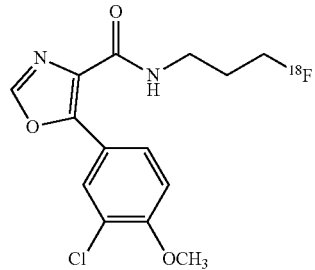
(29)
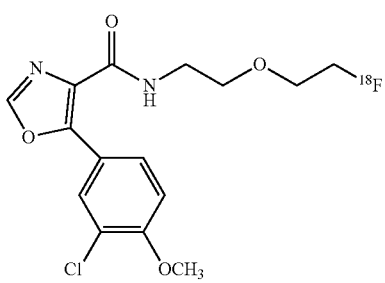
(30)
(31)

(32)
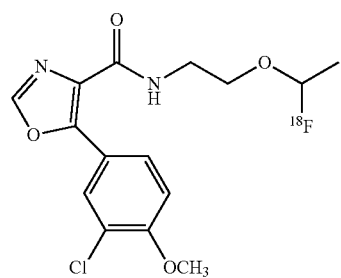
(33)
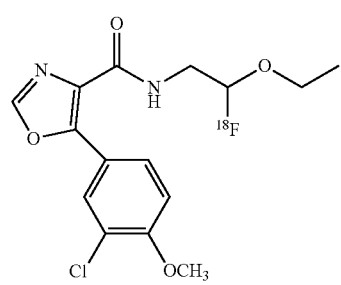
1p;2p
(34)
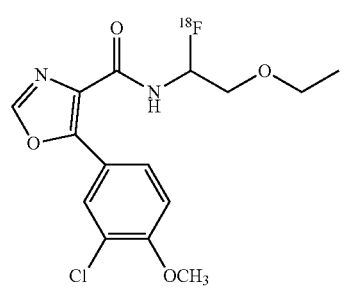
(35)
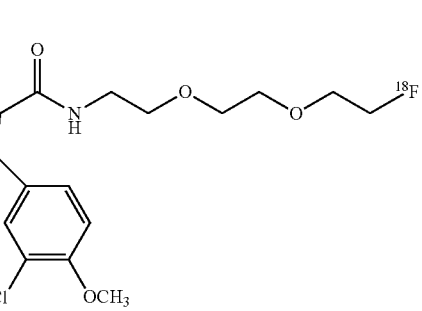
(36)
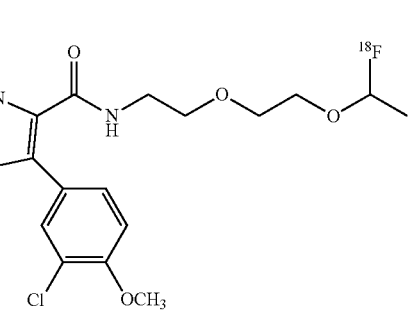
(37)
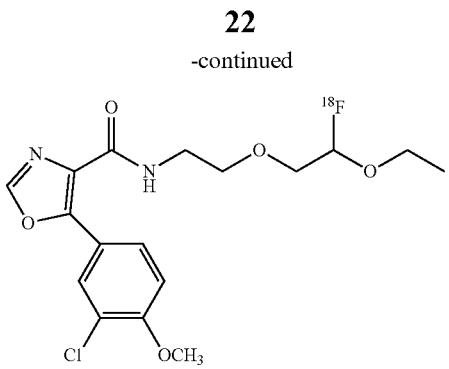
(38)
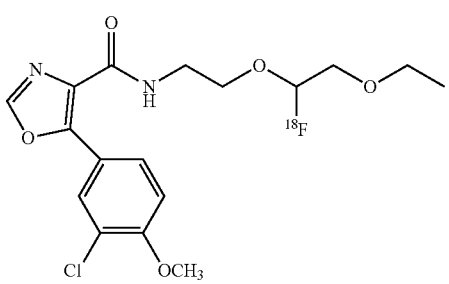
(39)
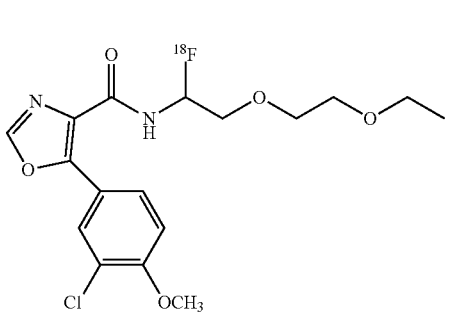
(40)
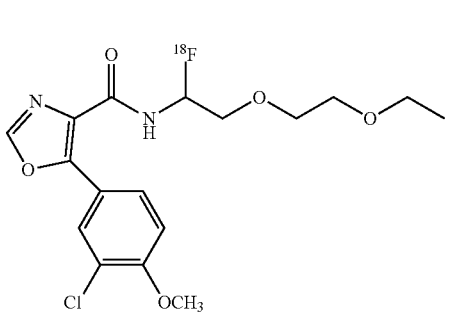
(41)
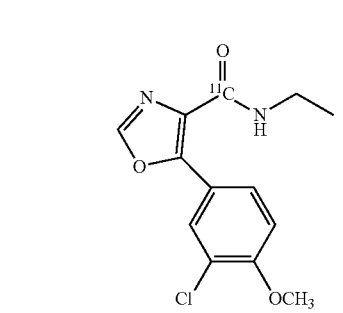

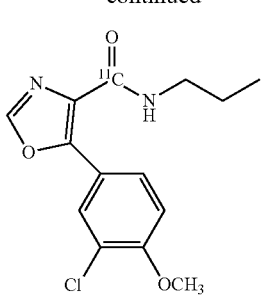
(42)

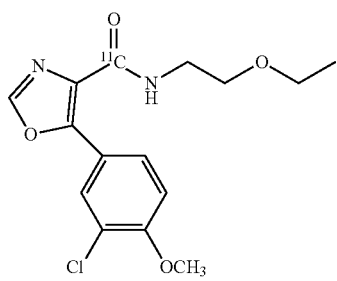
(43)

and

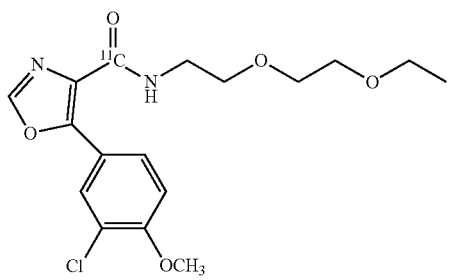
(44)

or a salt thereof.

In some embodiments, the radiolabelled compound of Formula I is of formula (2):

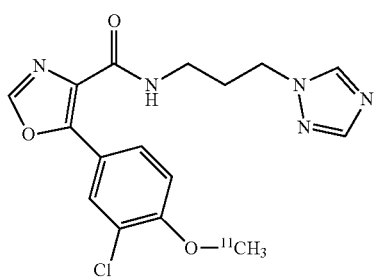
(2)

or a salt thereof.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

As used herein, the phrase "optionally substituted" means unsubstituted or substituted. As used herein, the term "substituted" means that a hydrogen atom is removed and replaced by a substituent. It is understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms. In some embodiments, the $C_{n-m}$ alkyl group comprises at least one radioisotope. In some embodiments, the $C_{n-m}$ alkyl group comprises at least one positron emitting radioisotope. In some embodiments, the $C_{n-m}$ alkyl group comprises at least one $^{11}C$ radioisotope.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms. In some embodiments, the $C_{n-m}$ alkylene group comprises at least one radioisotope. In some embodiments, the $C_{n-m}$ alkylene group comprises at least one positron emitting radioisotope. In some embodiments, the $C_{n-m}$ alkylene group comprises at least one $^{11}C$ radioisotope.

As used herein, the term "$C_{n-m}$ alkoxy", employed alone or in combination with other terms, refers to a group of formulae "—O-alkyl", "—(O-alkylene)$_p$—", or "-(alkylene-O)$_p$—, wherein the alkyl or alkylene group has n to m carbons and p is an integer from 1 to 6. Example alkoxy groups include methoxy, ethoxy, propoxy (e.g., n-propoxy and isopropoxy), tert-butoxy, —(CH$_2$OCH$_2$OCH$_2$)—, —(CH$_2$CH$_2$OCH$_2$CH$_2$O)—, —(OCH$_2$)—, —(OCH$_2$OCH$_2$CH$_2$)—, —(CH$_2$CH$_2$OCH$_2$CH$_2$O)—, —(CH$_2$CH$_2$OCH$_2$CH$_2$OCH$_2$CH$_2$)— and the like. In some embodiments, the alkyl or alkylene group has 1 to 6, 1 to 4, or 1 to 3 carbon atoms. In some embodiments, the $C_{n-m}$ alkoxy group comprises at least one radioisotope. In some embodiments, the $C_{n-m}$ alkoxy group comprises at least one positron emitting radioisotope. In some embodiments, the $C_{n-m}$ alkoxy group comprises at least one $^{11}C$ radioisotope.

As used herein, "halo" refers to F, Cl, Br, or I. In some embodiments, a halo is F, Cl, or I. In some embodiments, the halo group is a positron emitting radioisotope. In some embodiments, the halo is an $^{18}F$ or $^{123}I$ radioisotope. In some embodiments, the halo group is a gamma emitting radioisotope. In some embodiments, the halo group is a gamma emitting radioisotope selected from $^{123}I$, $^{125}I$, and $^{131}I$.

As used herein, "$C_{n-m}$ haloalkoxy" refers to a group of formulae "—O-haloalkyl", "—(O-haloalkylene)$_p$—", or "-(haloalkylene-O)$_p$—", wherein the alkyl or alkylene group has n to m carbons and p is an integer from 1 to 6. Example haloalkoxy groups include, but are not limited to, OCF$_3$, OCH$_2$CH$_2$F, OCH$_2$F, —CH$_2$CH$_2$OCH$_2$CH$_2$F, —CH$_2$CH$_2$OCH$_2$CH$_2$OCH$_2$CH$_2$F, OCl$_3$, OCH$_2$I, OCH$_2$CH$_2$I, —CH$_2$CH$_2$OCH$_2$CH$_2$I, —CH$_2$CH$_2$OCH$_2$CH$_2$OCH$_2$CH$_2$I, and the like. In some embodiments, the haloalkoxy group is fluorinated only. In some embodiments, the alkyl or alkylene group has 1 to 6, 1 to 4, or 1 to 3 carbon atoms. In some embodiments, the $C_{n-m}$ haloalkoxy group comprises at least one radioisotope. In some embodiments, the $C_{n-m}$ haloalkoxy group comprises at least one positron emitting radioisotope. In some embodiments, the $C_{n-m}$ haloalkoxy group comprises at least one positron emitting radioisotope selected from $^{11}C$, $^{18}F$, and $^{124}I$. In some embodiments, the $C_{n-m}$ haloalkoxy group comprises at least one gamma emitting radioisotope. In some embodiments, the $C_{n-m}$ haloalkoxy group comprises at least one gamma emitting radioisotope selected from $^{123}I$, $^{125}I$, and $^{131}I$.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. In some embodiments, the $C_{n-m}$ haloalkyl group comprises at least one radioisotope. In some embodiments, the $C_{n-m}$ haloalkyl group comprises at least one positron emitting radioisotope. In some embodiments, the $C_{n-m}$ haloalkyl group comprises at least one positron emitting radioisotope selected from $^{11}C$, $^{18}F$, and $^{124}I$. In some embodiments, the $C_{n-m}$ haloalkyl group comprises at least one gamma emitting radioisotope. In some embodiments, the $C_{n-m}$ haloalkyl group comprises at least one gamma emitting radioisotope selected from $^{123}I$, $^{125}I$, and $^{131}I$.

As used herein, the term "$C_{n-m}$ haloalkylene", employed alone or in combination with other terms, refers to a divalent haloalkyl linking group having n to m carbons. In some embodiments, the alkylene moiety contains 2 to 6, 2 to 4, 2 to 3, 1 to 6, 1 to 4, or 1 to 2 carbon atoms. In some embodiments, the $C_{n-m}$ haloalkylene group comprises at least one radioisotope. In some embodiments, the $C_{n-m}$ haloalkylene group comprises at least one positron emitting radioisotope. In some embodiments, the $C_{n-m}$ haloalkylene group comprises at least one positron emitting radioisotope selected from $^{11}C$, $^{18}F$, and $^{124}I$. In some embodiments, the $C_{n-m}$ haloalkylene group comprises at least one gamma emitting radioisotope. In some embodiments, the $C_{n-m}$ haloalkylene group comprises at least one gamma emitting radioisotope selected from $^{123}I$, $^{125}I$, and $^{131}I$.

As used herein, the term "$C_{n-m}$ alkylthio", employed alone or in combination with other terms, refers to a group of formula -alkyl-SH, wherein the alkyl group has n to m carbons. Example alkylthio groups include methylthio, ethylthio, n-propylthio, tert-butylthio, and the like. In some embodiments, the alkyl moiety has 1 to 6, 1 to 4, or 1 to 3 carbon atoms. In some embodiments, the $C_{n-m}$ alkylthio group comprises at least one radioisotope. In some embodiments, the $C_{n-m}$ alkylthio group comprises at least one positron emitting radioisotope. In some embodiments, the $C_{n-m}$ alkylthio group comprises at least one positron emitting radioisotope selected from $^{11}C$.

As used herein, the term "hydroxy" refers to a group of formula —OH.

The term "compound" as used herein is meant to include all stereoisomers, geometric isomers, and tautomers of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The present application further provides salts of the radiolabelled compounds provided herein.

All compounds and salts thereof can be found together with other substances such as water and solvents (e.g. hydrates and solvates) or can be isolated.

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to, chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluormethansulfonate, ethanesulfonate, benzenesulfonate, p-toluenesulfonate, p-trifluoromethylbenzenesulfonate, hydroxide, aluminates and borates. Exemplary cations include, but are not limited, to monovalent alkali metal cations, such as lithium, sodium, potassium and cesium, and divalent alkaline earth metals, such as beryllium, magnesium, calcium, strontium and barium. Also included are transition metal cations, such as gold, silver, copper and zinc, as well as non-metal cations, such as ammonium salts. The salts can be pharmaceutically acceptable.

Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred.

The term "pharmaceutically-acceptable salt" refers to salts which possess toxicity profiles within a range that affords utility in pharmaceutical applications. Pharmaceutically unacceptable salts may nonetheless possess properties such as high crystallinity, which may render them useful, e.g., in processes of synthesis, purification or formulation of compounds described herein. In general the useful properties of the compounds described herein do not depend on whether the compound is or is not in a salt form, so unless clearly indicated otherwise (such as specifying that the compound should be in "free base" or "free acid" form), reference in the specification to a compound should be understood as including salt forms of the compound, whether or not this is explicitly stated. Preparation and selection of suitable salt forms is described in *Handbook of Pharmaceutical Salts: Properties, Selection, and Use* By P. H. Stahl and C. G. Wermuth (Wiley-VCH 2002).

In some embodiments, the radiolabelled compounds provided herein, or salts thereof, are substantially isolated. By "substantially isolated" is meant that the radiolabelled compound is at least partially or substantially separated from the environment in which it was formed or detected. Partial separation can include, for example, a composition enriched in the radiolabelled compounds provided herein. Substantial separation can include compositions containing at least about 50%, at least about 60%, at least about 70%, at least about 80%, at least about 90%, at least about 95%, at least about 97%, or at least about 99% by weight of the radiolabelled compounds provided herein, or salt thereof. Methods for isolating compounds and their salts are routine in the art.

II. Synthesis

As will be appreciated, the compounds provided herein (i.e., unlabelled compounds or radiolabelled compounds of Formula I), including salts thereof, can be prepared using organic synthesis techniques and can be synthesized according to any of numerous possible synthetic routes. For example, the unlabelled compounds provided herein (i.e., unlabelled compounds of Formula I and salts thereof) may be prepared by amide coupling according to the procedure shown in Scheme 1. The procedure uses an amide coupling agent such as carbodiimides and triazoles, e.g., NN'-dicyclohexylcarbodiimide, N,N,N',N'-Tetramethyl-O-(benzotriazol-1-yl)uronium tetrafluoroborate (TBTU) or N,N'-diisopropylcarbodiimide, 1-[Bis(dimethylamino)methylene]-1H-1,2,3-triazolo [4,5-b]pyridinium 3-oxide hexafluorophosphate) (HATU). Typically, a base such as triethylamine, N,N-diisopropylethylamine, pyridine, or 4-(N,N-dimethylamino)pyridine is also included. Radiolabelled compounds can be prepared by analogous procedures with radiolabelled starting materials or intermediates.

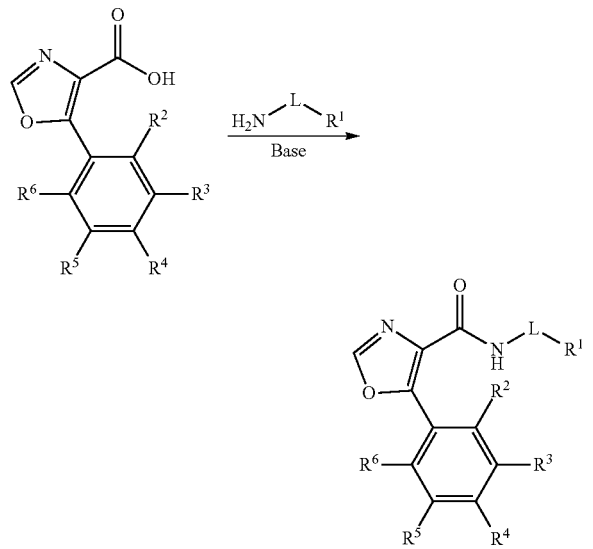

Scheme 1

The radiolabelled compounds provided herein (i.e., radiolabelled compounds of Formula I and salts thereof) may be prepared, for example, according to the procedure shown in Scheme 2. The hypervalent iodine(III) ylides starting material (e.g., wherein the ylide is substituted at any of $R^2$, $R^3$, $R^4$, $R^5$, or $R^6$) enables a one-step radiofluorination of non-activated and sterically-demanding (hetero)aromatic rings using [$^{18}$F]fluoride, thereby allowing the design of radiotracers without the need for electron withdrawing arenes or prosthetic groups that mandate multi-step synthesis with $^{18}$F. Additional examples of the procedure shown in Scheme 2 may be found, for example, in International Patent Application No. WO 2015/134923, the disclosure of which is incorporated herein by reference in its entirety.

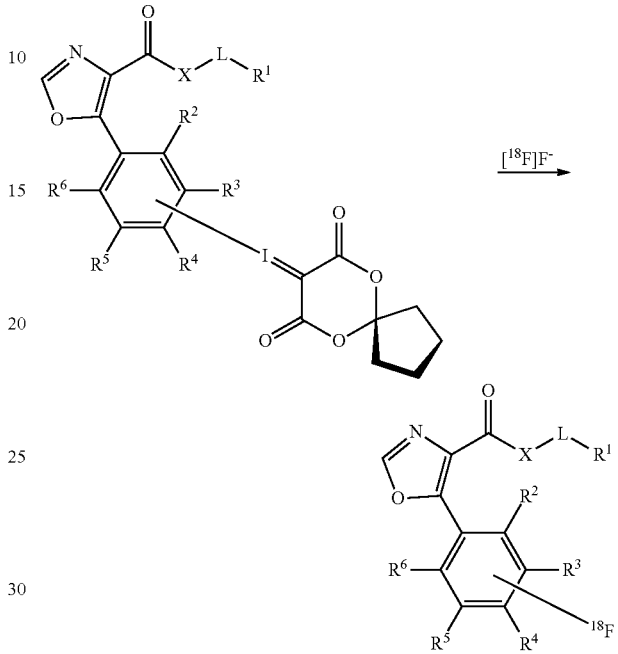

Scheme 2

The radiolabelled compounds provided herein may also be prepared, for example, according to the procedure shown in Scheme 3.

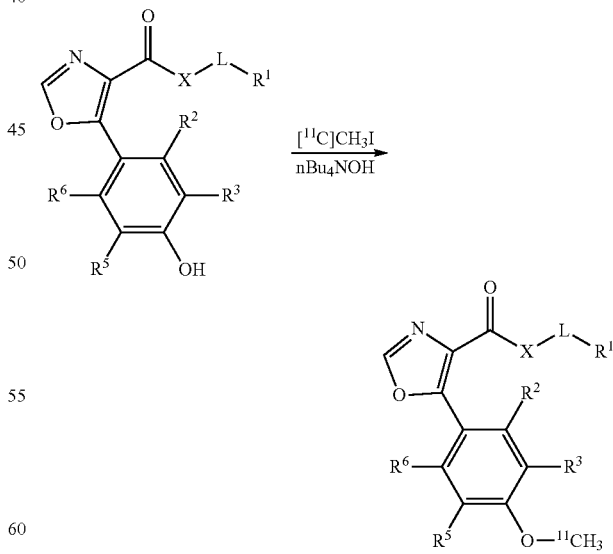

Scheme 3

The radiolabelled compounds provided herein may also be prepared, for example, according to the procedure shown in Scheme 4. Radiolabelled compounds provided herein can be prepared, for example, using [$^{11}$C]CO$_2$ directly from the cyclotron to label carbonyl groups, which enables the formation of highly functionalized substrates. See Rotstein et al., Chem. Commun., 2013, 49, 5621-29.

Scheme 4

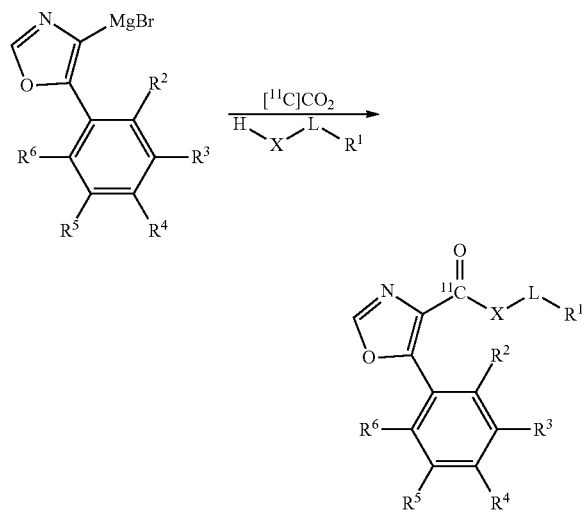

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

III. Methods of Use and Administration

The present disclosure provides methods of imaging tissue, cells, or a subject using the radiolabelled compounds of the present disclosure; methods of imaging a disease and/or related biological events, using a radiolabelled compounds of the present disclosure; methods of diagnosing a disease or related biological events using a probe of the present disclosure; methods of monitoring the progress of a disease or related biological events using a probe of the present disclosure; and the like. Embodiments of the present disclosure can be used to image, detect, study, monitor, evaluate, assess, and/or screen, the disease and/or related biological events, in particular, diseases associated with GSK3, including GSK3α and/or GSK3β using the radiolabelled compounds of the present disclosure.

The present application further provides a method of imaging GSK3 kinase in a cell or tissue sample. In some embodiments, the method comprises contacting the cell or tissue sample with a radiolabelled compound provided here, or a salt thereof, and subsequently imaging the cell or tissue sample. In some embodiments, the method comprises repeatedly imaging the cell or tissue sample after contacting the cell or tissue sample with the radiolabelled compound.

The present application further provides a method of imaging GSK3 kinase in a subject. In some embodiments, the method comprises administering to the subject a radiolabelled compound provided herein, or a salt thereof, and subsequently imaging the subject. As used herein, the term "subject," refers to any animal, including mammals. Example subjects include, but are not limited to, mice, rats, other rodents, rabbits, dogs, cats, swine, cattle, sheep, horses, primates, and humans. In some embodiments, the subject is a human.

The radiolabelled compounds have high uptake for imaging GSK3. The standardized uptake value (SUV) is often used in positron emission tomography (PET) imaging for a (semi)quantitative analysis. The SUV is the ratio of the image derived radioactivity concentration $c_{img}$ and the whole body concentration of the injected radioactivity $c_{inj}$:

$$SUV = \frac{C_{img}}{C_{inj}}$$

In some embodiments, the GSK-3 kinase comprises GSK-3α and GSK-3β.

In some embodiments, the imaging comprises a minimally invasive imaging technique. As used herein, the term "minimally invasive imaging technique" is an imaging technique employing the use of an internal probe or injection of a radiolabelled compound via syringe into a cell or tissue sample or a subject. In some embodiments, the imaging is PET imaging. In some embodiments, the imaging is SPECT imaging.

In general, the radiolabelled compounds can be used in imaging cancer and/or diseases with GSK3, including GSK3α and/or GSK3β. For example, the radiolabelled compound can be administered to a subject in an amount effective to result in uptake of the radiolabelled compound into the disease or tissue of interest. The subject is then introduced to an appropriate imaging system (e.g., PET system) for a certain amount of time. The cells or tissue that takes up the probe could be detected using the imaging system. The location of the detected signal from the probe can be correlated with the location of the disease(s).

The imaging can be repeated at determined intervals so that the location and/or extent of the disease can be monitored as a function of time and/or treatment. In particular, the radiolabelled compound can find use in a host undergoing chemotherapy, for example, or other treatment (e.g., using a drug), to aid in visualizing the response of a disease to the treatment. In this embodiment, imaging is typically performed prior to treatment, and periodically during therapy.

The radiolabelled compounds described herein can also be used as a screening tool in vitro to select compounds for use in treating diseased tissue or cells, wherein the disease is one that is associated with activity of GSK-3 kinase (including GSK-3α and/or GSK-3β). The disease can be monitored by incubating the cells with the disease with the radiolabelled compound during or after incubation with one or more candidate drugs. The ability of a drug compound to affect the disease can be imaged over time using the radiolabelled compound.

In some embodiments, the imaging is PET imaging and the compound is:

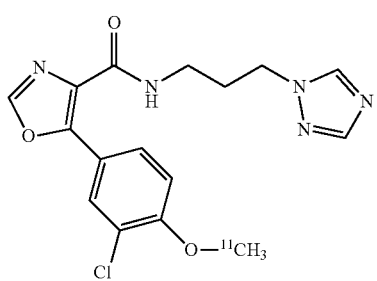

(2)

or a salt thereof.

The radiolabelled compounds provided herein can be administered in the form of compositions (e.g., pharmaceutical compositions) comprising a radiolabelled compound provided herein, or a salt thereof, in combination with one or more carriers (excipients). In making the compositions provided herein, the radiolabelled compound can be mixed with an excipient or diluted by an excipient. When the excipient serves as a diluent, it can be a liquid material, which acts as a vehicle, carrier, or medium for the radiolabelled compound. These compositions can be prepared as described herein or elsewhere, and can be administered by a variety of routes, such as parenteral administration. Parenteral administration includes, but is not limited to, intravenous, intraarterial, subcutaneous, intraperitoneal intramuscular or injection or infusion; or intracranial, (e.g., intrathecal or intraventricular) administration. Parenteral administration can be in the form of a single bolus dose, or may be, for example, by a continuous perfusion pump. The excipients used to form such compositions are preferably pharmaceutically acceptable, which refers to any carrier, diluent or excipient which is compatible with the other ingredients of the formulation and not deleterious to the recipient.

In some embodiments, the radiolabelled compounds provided herein, or salts thereof, are suitable for parenteral administration. In some embodiments, the compounds provided herein are suitable for intravenous administration. Conventional pharmaceutical carriers, aqueous or oily bases, and the like may be necessary or desirable. These compositions can be sterilized by conventional sterilization techniques, or may be sterile filtered.

The pH of the compound preparations typically will be between 3 and 11, more preferably from 5 to 9 and most preferably from 7 to 8.

Examples of diseases associated with GSK-3 kinase activity, and for which the methods described above may be useful include: type I and type II diabetes, obesity, ischemia, cancer, sepsis, colitis and neurological disorders, immune disorders, metabolic disorders (atherosclerosis, diabetes, and heart disease), and neurological disorders.

Examples of cancers include cancers include bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer and testicular cancer. More particularly, the cancers that include:

1) Breast cancers, including, e.g., ER breast cancer, ER⁻ breast cancer, her2⁻ breast cancer, her2⁺ breast cancer, stromal tumors such as fibroadenomas, phyllodes tumors and sarcomas and epithelial tumors such as large duct papillomas; carcinomas of the breast including in situ (non-invasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative (ER⁻), progesterone receptor negative, and her2 negative (her2⁻). In some embodiments, the breast cancer may have a high risk Oncotype score.

2) Cardiac cancers, including, e.g., sarcoma, e.g., angiosarcoma, fibrosarcoma, rhabdomyosarcoma, and liposarcoma; myxoma; rhabdomyoma; fibroma; lipoma and teratoma.

3) Lung cancers, including, e.g., bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, e.g., cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, e.g., cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, e.g., hepatoma, e.g., hepatocellular carcinoma; cholangiocarcinoma; hepatoblastoma; angiosarcoma; hepatocellular adenoma; and hemangioma.

7) Bone cancers, including, e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, e.g., cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, e.g., cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, e.g., cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia.

11) Skin cancers, including, e.g., malignant melanoma, basal cell carcinoma, squamous cell carcinoma, Kaposi's sarcoma, moles dysplastic nevi, lipoma, angioma, dermatofibroma, keloids, and psoriasis.

12) Adrenal gland cancers, including, e.g., neuroblastoma.

13) Pancreatic cancers, including, e.g., exocrine pancreatic cancers such as adenocarcinomas (M8140/3), adenosquamous carcinomas, signet ring cell carcinomas, hepatoid carcinomas, colloid carcinomas, undifferentiated carcinomas, and undifferentiated carcinomas with osteoclast-like giant cells; and exocrine pancreatic tumors.

Examples of neurological disorders include Alzheimer's disease, amyotrophic lateral sclerosis, bipolar disorder, mood disorders, Huntington's disease, Parkinson's disease, schizophrenia, progressive supranuclear palsy, dementia pugilistica, chronic traumatic encephalopathy, frontotemporal dementia or Parkinsonism linked to chromosome 17, however without detectable β-amyloid plaques, Lytico-Bodig disease, tangle-predominant dementia, ganglioglioma and gangliocytoma, meningioangiomatosis, subacute sclerosing panencephalitis, lead encephalopathy, tuberous sclerosis, Hallervorden-Spatz disease, lipofuscinosis, Pick's disease, corticobasal degeneration, and Argyrophilic grain disease (AGD).

Specifically for neurodegenerative diseases, molecular imaging of GSK-3 can indicate target engagement by GSK-3 therapeutics and offer a path to diagnostic agents that not only correlates with early cognitive impairment, but also increased tau yperphosphorylation, increased amyloid-β production and local plaque-associated glial-mediated inflammatory responses; all of which are hallmarks of Alzheimer's disease and non-Alzheimer's tauopathies.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. Prediction of Blood Brain Barrier Penetration

Blood brain barrier penetration by compound (1) was predicted using multi-parameter optimization (MPO; see e.g., Wager et al., ACS Chemical Neuroscience, 2010, 1:435). The MPO total scale of compound (1) (5.65 out of 6.00) is within the range of CNS drugs with reasonable brain penetration. Compound (1) demonstrates favorable properties as a CNS inhibitor in lipophilicity (clogP and clogD), topological polar surface area (TPSA), molecular weight (MW), hydrogen bonding (HBD) and acidity (pKa), as shown in Table 1.

TABLE 1

MPO Total Score of Compound (1)
MPO Total Score of Compound (1): 5.65 out of 6.00

| Entry | Value | MPO Score | Entry | Value | MPO Score |
|---|---|---|---|---|---|
| cLogP | 1.47 | 1.00 | MW | 361.79 | 1.00 |
| cLogD | 0.0 | 1.00 | HBD | 1 | 0.83 |
| TPSA | 87.88 | 1.00 | pKa | 8.36 | 0.82 |

Example 2. Radiochemistry Protocols

To determine the in vivo distribution and pharmacokinetic profile of compound (1) in higher species of nonhuman primates, compound (1) was radiolabelled with carbon-11 and the permeability of compound (1) was evaluated in the living brain using positron emission tomography. [$^{11}$C] labelled compound (1) was synthesized in 5% uncorrected radiochemical yield (relative to [$^{11}$C]CO$_2$) by reaction of the corresponding phenolic precursor in the presence of tetrabutylammonium hydroxide in DMF with [$^{11}$C]CH$_3$I with specific activity >2 Ci/µmol (n=15).

A. Preparation of [$^{11}$C] Labelled GSK Ligand N-(3-(1H-1,2,4-Triazol-1-yl)propyl)-5-(3-chloro-4-[$^{11}$C]methoxyphenyl)oxazole-4-carboxamide (2)

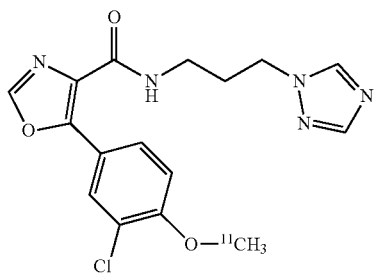

(2)

The radiosynthesis of [$^{11}$C] labelled compound (1) (PF-367) (compound (2)) was carried out using the "loop" method (see e.g. Wilson et al., *Journal of Labelled Compounds and Radiopharmaceuticals*, 2009, 52:490-492). Briefly, a pre-mixed solution of the phenolic precursor, tetrabutylammonium hydroxide in dry DMF (vide infra) was loaded on the HPLC loop of the GE Tracerlab FX$_{F-N}$ module. [$^{11}$C]CH$_3$I was delivered to the HPLC loop in a stream of nitrogen gas at a flow rate of 10 mL/min. Five minutes after the end of the radioactivity delivery, the reaction mixtures were injected onto a HPLC column (Phenomenex Luna C$_{18}$, 250×10 mm, 10 µm) and eluted with 40:60 CH$_3$CN/0.1N ammonium formate at a flow rate of 5 mL/min. The eluent was monitored by UV ($\lambda$=254 nm) and radiochemical detectors connected in series. The retention time of [$^{11}$C] labelled compound (1) is 11 minutes. The product was diluted with 20 mL of sterile water for injection, USP. The diluted HPLC fraction was then loaded on an Oasis HLB light cartridge, then washed with 10 mL sterile water for injection, USP. The [$^{11}$C] labelled compound (1) was recovered in 1 mL dehydrated alcohol for injection, USP and 10 mL of 0.9% sodium chloride for injection, USP. The solution was transferred and passed through a 0.22 µm PALL sterilizing filter into a vented sterile 10 mL dose vial (Hospira).

B. Quality Control

To determine the identity of the [$^{11}$C] labelled compound (1), aliquots of the formulated product were injected onto an analytical HPLC system using a Phenomenex Synergi column, 150×4.6 mm, 4 µm and eluted with CH$_3$CN:H$_2$O+0.1 N ammonium formate (60/40) at a flow rate of 1 mL/min, monitored at $\lambda$=254 nm. The major radiochemical product was identified as [$^{11}$C] labelled compound (1) (t$_R$=~6.5 min), followed by co-injection with the reference standard, authentic compound (1). The radiochemical purity was >99% by radio-HPLC (Phenomenex Synergi column, 150× 4.6 mm, 4µ, CH$_3$CN:H$_2$O+0.1 N ammonium formate (60: 40), flow rate 1 mL/min). UV detector ($\lambda$=254 nm) was prior to radioactivity detector in series. Chemical purity was ≥95%. Specific activity was determined using [$^{11}$C] labelled compound (1) against a calibration curve prepared with a reference (unlabelled) sample of compound (1). Specific activity was ≥2 Ci per micromole at time of administration.

C. Determination of Log D$_{7.4}$ of [$^{11}$C] Labelled Compound (1)

The measurement of lipophilicity was carried out using literature procedure. Purified and reformulated [$^{11}$C] labelled compound (1) (~50 µL) was added to a separating funnel containing PBS buffer (pH 7.4) and 1-octanol (pre-saturated with PBS buffer) (~20 mL each). The octanol layer was collected and dispensed into 8 centrifuge tubes (2 mL each) containing PBS buffer (2 mL each). The tubes were mixed by vortex for 2 min and then centrifuged for 5 min. Approximately 0.5 mL of the octanol layer and 1.0 mL of the aqueous from each centrifuge tube was then transferred to pre-weighed test tubes (16 in total). The tubes were capped and assayed using an automated gamma counter. The tubes were then uncapped and weighed to determine the total volume of the liquid in each. The log D$_{7.4}$ of [$^{11}$C] labelled compound (1) was determined to be 2.14 (n=7).

Example 3. PET Imaging Studies Animals

In vivo assessments of [$^{11}$C] labelled compound (1) were performed in animals and confirmed brain penetration and displaceable specific binding.

Bolus i.v. administration of [$^{11}$C]-labelled compound (1) to a rat (n=1) showed rapid uptake of the radioligand with a maximum uptake of about 1 SUV at 1-2 min. followed by rapid clearance. Results are shown in FIG. 1.

Bolus i.v. administration of [$^{11}$C]-labelled compound (1) in rhesus monkeys (5-7 mCi) reached a whole brain peak uptake (2 SUV) with fairly uniform brain distribution followed by a fast clearance (1 SUV at 40 min). Co-administration of [$^{11}$C]-labelled compound (1) and unlabelled compound (1) (0.1 mg/kg) showed increased peak uptake (3.5 SUV) and decreased binding (0.3 SUV at 40 min) in all brain regions. Liang et al., "Discovery of [$^{11}$C]PF-367 for neuroimaging of glycogen synthase kinase 3", *J. Nucl. Med.*, 2015, 56(Supp. 3), 491.

Protocols were approved by the Institutional Animal Care and Use Committee at Massachusetts General Hospital

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A radiolabelled compound of Formula I:

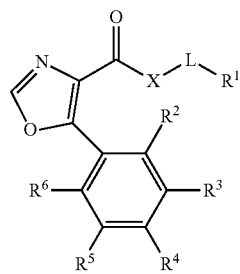

or a salt thereof, wherein:
X is selected from the group consisting of O and $NR^N$;
$NR^N$ is selected from the group consisting of H, $C_{1-6}$ alkyl, and $C_{1-6}$ haloalkyl;
L is selected from the group consisting of $C_{1-6}$ alkylene and $C_{1-6}$ haloalkylene;
$R^1$ is selected from the group consisting of H, halo, $C_{1-6}$ alkyl, $C_{1-6}$ haloalkyl, $C_{1-6}$ alkoxy, $C_{1-6}$ haloalkoxy, and 5-10 membered heteroaryl;
$R^2$, $R^3$, $R^4$, $R^5$, and $R^6$ are each independently selected from the group consisting of H, halo, $C_{1-6}$ alkyl, $C_{1-6}$ haloalkyl, hydroxy, $C_{1-6}$ alkoxy, $C_{1-6}$ haloalkoxy, and $C_{1-6}$ alkylthio; and
wherein the compound of Formula I is radiolabelled.

2. The radiolabelled compound or salt thereof of claim 1, wherein the compound is radiolabelled with a positron emitting radioisotope selected from $^{11}C$, $^{13}N$, $^{15}O$, $^{18}F$ and $^{124}I$; or a gamma emitting radioisotope selected from $^{123}I$, $^{125}I$, and $^{131}I$.

3. The radiolabelled compound or salt thereof of claim 1, wherein X is $NR^N$.

4. The radiolabeled compound or salt thereof of claim 3, wherein $R^N$ is H.

5. The radiolabelled compound or salt thereof of claim 4, wherein L is trimethylene (—$CH_2CH_2CH_2$—).

6. The radiolabelled compound or salt thereof of claim 1, wherein $R^1$ is selected from the group consisting of halo, $C_{1-6}$ haloalkyl, $C_{1-6}$ haloalkoxy, and a 5-6 membered heteroaryl group.

7. The radiolabelled compound or salt thereof of claim 1, wherein $R^2$ is hydrogen, $R^3$ is hydrogen or halo, and $R^4$ is selected from the group consisting of hydrogen, halo, hydroxy, $C_{1-6}$ alkoxy, and $C_{1-6}$ haloalkoxy, $R^5$ is hydrogen or halo, and $R^6$ is hydrogen.

8. The radiolabelled compound or salt thereof of claim 7, wherein $R^4$ is a $[^{11}C]$-radiolabelled $C_{1-6}$ alkoxy.

9. The radiolabeled compound or salt thereof of claim 8, wherein $R^4$ is —$O^{11}CH_3$.

10. The radiolabelled compound or salt thereof of claim 1, wherein the compound is a compound of Formula III:

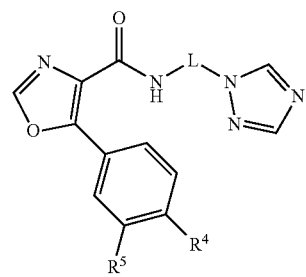

wherein:
L is selected from the group consisting of $C_{1-6}$ alkylene and $C_{1-6}$ haloalkylene;
$R^4$ and $R^5$ are each independently selected from the group consisting of halo, $C_{1-6}$ alkyl, $C_{1-6}$ haloalkyl, hydroxy, $C_{1-6}$ alkoxy, $C_{1-6}$ haloalkoxy, and $C_{1-6}$ alkylthio.

11. The radiolabelled compound or salt thereof of claim 1, wherein the compound is a compound of the following formula:

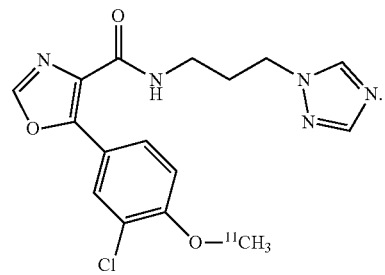 [SMILES: [11CH3]Oc1ccc(-c2ocnc2C(=O)NCCCn2cncn2)cc1Cl]

12. A method of imaging GSK-3 kinase in a cell or tissue sample, the method comprising contacting the cell or tissue sample with the radiolabelled compound or salt thereof of claim 1, and subsequently imaging the cell or tissue sample.

13. A method of imaging GSK-3 kinase in a subject, comprising administering to the subject the radiolabelled compound or salt thereof of claim 1, and subsequently imaging the subject.

14. The method of claim 13, wherein the imaging is PET imaging or SPECT imaging.

15. A method of imaging GSK-3 kinase in a subject, comprising administering to the subject the radiolabelled compound or salt thereof of claim 11, and subsequently imaging the subject by PET imaging.

* * * * *

UNITED STATES PATENT AND TRADEMARK OFFICE
CERTIFICATE OF CORRECTION

PATENT NO. : 10,280,152 B2
APPLICATION NO. : 15/563022
DATED : May 7, 2019
INVENTOR(S) : Neil Vasdev and Huan Steven Liang Page 1 of 1

It is certified that error appears in the above-identified patent and that said Letters Patent is hereby corrected as shown below:

In the Claims

In Column 37, Line 32 (approx.), in Claim 2, delete "$^{18}$F" and insert -- $^{18}$F, --.

Signed and Sealed this
Twenty-seventh Day of August, 2019

Andrei Iancu
*Director of the United States Patent and Trademark Office*